(12) United States Patent
Lin

(10) Patent No.: US 8,091,183 B2
(45) Date of Patent: Jan. 10, 2012

(54) WIRE GRIP

(75) Inventor: Chu Geng Lin, Tu-Cheng (TW)

(73) Assignee: Cheng Uei Precision Industry Co., Ltd., Tu-Cheng, Taipei Hsien (TW)

(*) Notice: Subject to any disclaimer, the term of this patent is extended or adjusted under 35 U.S.C. 154(b) by 722 days.

(21) Appl. No.: 12/222,395

(22) Filed: Aug. 8, 2008

(65) Prior Publication Data
US 2010/0031480 A1    Feb. 11, 2010

(51) Int. Cl.
*G01N 3/04* (2006.01)
(52) U.S. Cl. .................................. 24/115 J; 73/858
(58) Field of Classification Search .............. 73/828, 73/826, 829, 831, 833, 858, 856, 860; 24/115 J
See application file for complete search history.

(56) References Cited

U.S. PATENT DOCUMENTS

| | | | | |
|---|---|---|---|---|
| 2,327,139 A | * | 8/1943 | Scott | 73/858 |
| 3,171,277 A | * | 3/1965 | Gloor | 73/858 |
| 3,528,283 A | * | 9/1970 | Gadd | 73/858 |

FOREIGN PATENT DOCUMENTS

| | | | |
|---|---|---|---|
| FR | 2655423 A1 | * | 6/1991 |
| GB | 2083233 A | * | 3/1982 |
| JP | 61281936 A | * | 12/1986 |
| JP | 04301539 A | * | 10/1992 |
| JP | 11118688 A | * | 4/1999 |

* cited by examiner

*Primary Examiner* — James Brittain
(74) *Attorney, Agent, or Firm* — Cheng-Ju Chiang

(57) ABSTRACT

A wire grip is adapted for fastening a wire and mounted to a tension device which pulls the wire grip to produce a pulling force to the wire. The wire grip includes a basic body and a capstan. The capstan is slidably mounted to the basic body for fastening an end portion of the wire and enabling the wire to be wrapped thereon. The capstan is movable in a direction relative to an axis thereof whereby to ensure the pulling force provided by the tension device is in alignment direction with the pulling force received by a middle portion of the wire.

4 Claims, 3 Drawing Sheets

WIRE GRIP

BACKGROUND OF THE INVENTION

1. Field of the Invention

The present invention relates to a wire grip, and more particularly to a wire grip mounted to a tension device for fastening a wire.

2. The Related Art

Conventionally, a wire is fastened in a tension device for testing some tension parameters of the wire. The tension device includes two wire grips. The wire grip has a capstan. Two ends of the wire are coiled around the two capstans respectively so that the middle portion of the wire between the two wire grips is tightened when the wire grips are pulled towards the reverse direction. At this time, the direction of the pulling force is consistent with the axis of the wire so that the pulling force of the tension device is transferred completely to the wire by the wire grips. Thus the tension parameter about the wire is enabled to be obtained from the tension device exactly.

However, the tension device is designed to test the wire with a predetermined diameter. That is, supposing the tension device is designed to test a thin wire. When a thick wire is fastened between the wire grips of the tension device, the tension parameters obtained from the tension device are not exact because the axis of the thick wire does not conform with the direction of the pulling force applied by the tension device. Therefore, it is desirable to provide a wire grip which is able to be adjusted so that the axis of the wire is in line with pulling force provided by the tension device for fixing wires of different diameters.

SUMMARY OF THE INVENTION

Accordingly, an object of the present invention is to provide a wire grip capable of being adjusted to make the axis of a wire conform with a pulling force provided by the tension device for fixing wires of different diameters.

The wire grip is adapted for fastening a wire and mounted to a tension device which pulls the wire grip to produce a pulling force to the wire. The wire grip includes a basic body and a capstan. The capstan is slidably mounted to the basic body for fastening an end portion of the wire and enabling the wire to be wrapped thereon. The capstan is movable in a direction relative to an axis thereof whereby to ensure the pulling force provided by the tension device is in alignment direction with the pulling force received by a middle portion of the wire.

As described above, the capstan is movable in a direction relative to an axis thereof so as to adjust a middle portion of the wire in line with pulling force provided by the tension device when the diameter of the wire changes. Thus the wire grip is capable of fixing the wires of different diameters so that the tension device can test the wires of different diameters, which not only reduces the cost of manufacturing different wire grips, but also simplifies process of repetitious assembly and disassembly.

BRIEF DESCRIPTION OF THE DRAWINGS

The present invention will be apparent to those skilled in the art by reading the following description of an embodiment thereof, with reference to the attached drawings, in which.

DETAILED DESCRIPTION OF THE EMBODIMENT

Figure 1:
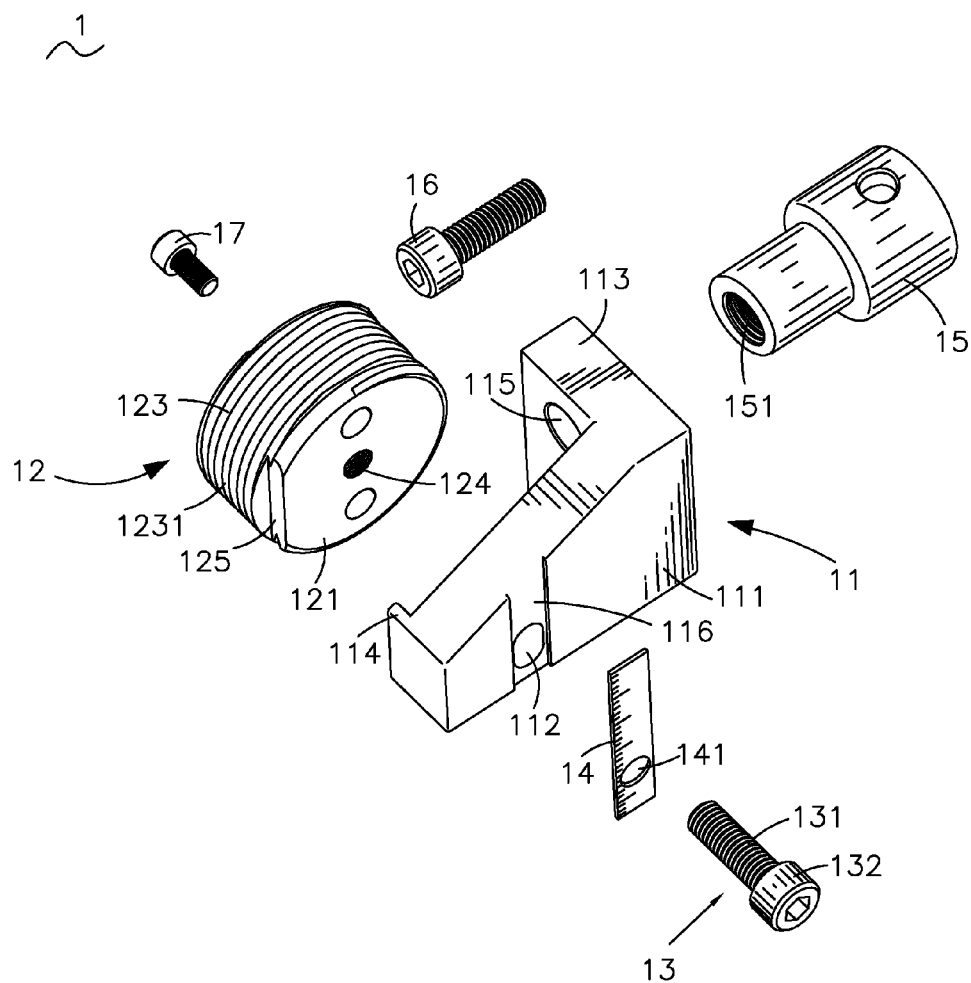
FIG. 1 is an exploded, perspective view of a wire grip of an embodiment according to the present invention.

With reference to FIG. 1, a wire grip 1 mounted on a tension device (not shown) includes a basic body 11, a capstan 12 and a fixing component 13 adapted for fastening the capstan 12 to the basic body 11.

The basic body 11 has a mounting plate 111 of taper shape, a fixing plate 113 intersecting with a wider end of the mounting plate 111 and a block 114 extending from the other end of the mounting plate 111, wherein the block 114 and the fixing plate 113 are located at a same side of the mounting plate 111. A surface of the mounting plate 111 opposite to the fixing plate 113 has a groove 116 near the narrower end thereof. The groove 116 parallels the fixing plate 113 and passes through the whole surface. The groove 116 has an adjusting hole 112 for receiving the fixing component 13. The adjusting hole 112 has a larger dimension in cross section than that of the fixing component 13 in a direction being parallel to the groove 116 for allowing the fixing component 13 to be movable therealong together with the capstan 12. The fixing plate 113 is rectangular. In this embodiment, the fixing plate 113 extends perpendicularly from the wider end of the mounting plate 111. The fixing plate 113 defines a fixing hole 115 thereon. The block 114 is smaller and narrower than the fixing plate 113 to show a bar shape.

Figure 2:
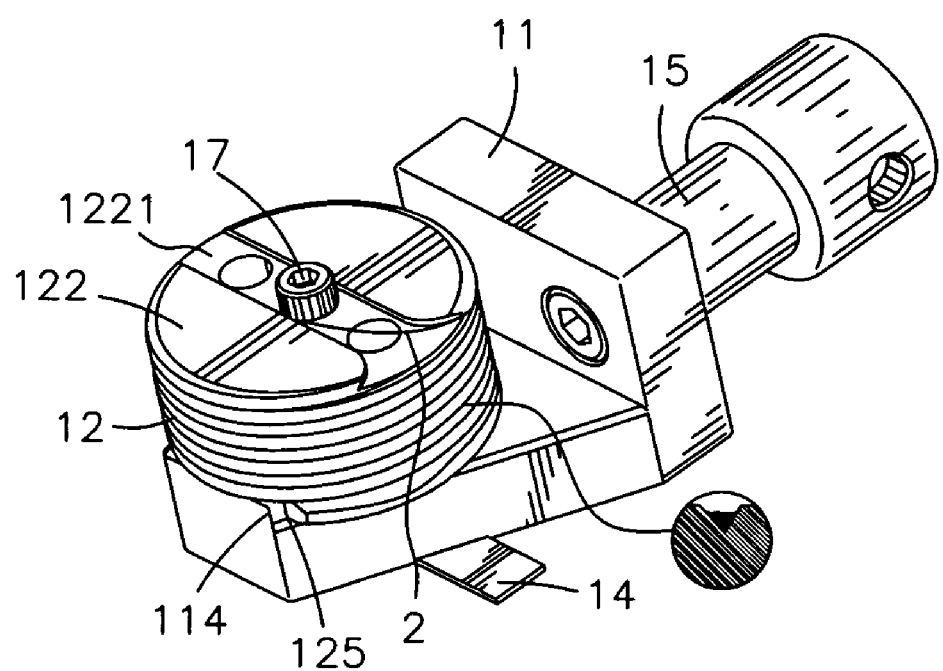
FIG. 2 is an assembled, perspective view of the wire grip shown in FIG. 1, wherein a wire is wrapped around a capstan of the wire grip.

Please referring to FIG. 1 and FIG. 2, the capstan 12 is cylindrical and defines a first surface 121, a second surface 122 opposite to the first surface 121 and a peripheral surface 123 connecting the first surface 121 and the second surface 122. The capstan has an installing hole 124 extending from a center of the first surface 121 to reach the second surface 122. The installing hole 124 is machined screw threads for connecting the fixing component 13. In this embodiment, because the capstan 12 is required to be fixed to the basic body 11 via the fixing component 13 and fixes a wire 2 thereon via a locating screw 17, the diameter of an end of the installing hole 124 adjacent to the first surface 121 is larger than that of the other end of the installing hole 124 for respectively engaging with the fix component 13 and the locating screw 17 at two opposite ends thereof. The first surface 121 is processed to form a gap 125 at the connection of the first surface 121 and the peripheral surface 123 for engaging with the block 114 to prevent the capstan 12 from rotating relevant to the basic body 11. The peripheral surface 123 is helically machined a leading slot 1231 for receiving the wire 2. In this embodiment, the cross-section of the leading slot 1231 is preferable to be shaped as triangle. Thus the wire 2 can be clamped in the leading slot 1231, which prevents the wire 2 from moving in the leading slot 1231 during the process of testing. The second surface 122 is opened a leading groove 1221 around the installing hole 124. The leading groove 1221 is strip-shaped with at least one end communicating with the leading slot 1231. Thus the wire 2 fixed between the locating screw 17 and the capstan 12 is wrapped in the leading slot 1231 through leading groove 1221 for avoiding the wire 2 moving.

The fixing component 13 includes a fixing portion 131 corresponding to the adjusting hole 112 and a stopping portion 132 disposed at an end of the fixing portion 131. The fixing portion 131 is rod-shaped and machined with screw threads for coupling with the installing hole 124. The stopping portion 132 is cylindrical with a diameter larger than that of the fixing portion 131. The fixing portion 131 passes through the adjusting hole 112 of the basic body 11 to connect with the installing hole 124 of the capstan 12 with the stopping portion 132 abutting an edge of the adjusting hole 112. Thus the basic body 11 is connected together with the capstan 12. Because the fixing portion 131 is capable of moving in the adjusting hole 112 along the extending direction of the groove 116 with the capstan 12, the wire 2 between the wire grips 1 can be adjusted a certain distance according to the change of the diameter thereof so as to conform with the pulling force provided by the tension device. In this embodiment, the fixing component 13 is a screw.

In this embodiment, the wire grip 1 further has a measuring plate 14 with the graduation. The measuring plate 14 is oblong and has an inserting hole 141 corresponding to the fixing portion 131 at one end thereof. The measuring plate 14 is received in the groove 116 and moved by the fixing portion 131 for indicating the moving distance. A holding component 15 is cylindrical and has a screw hole 151 at one end thereof. The holding component 15 is fixed together with the basic body 11 via a fixing screw 16 passing through the fixing hole 115 to connect with the screw hole 151. The other end of the holding component 15 is mounted to the tension device.

Figure 3:
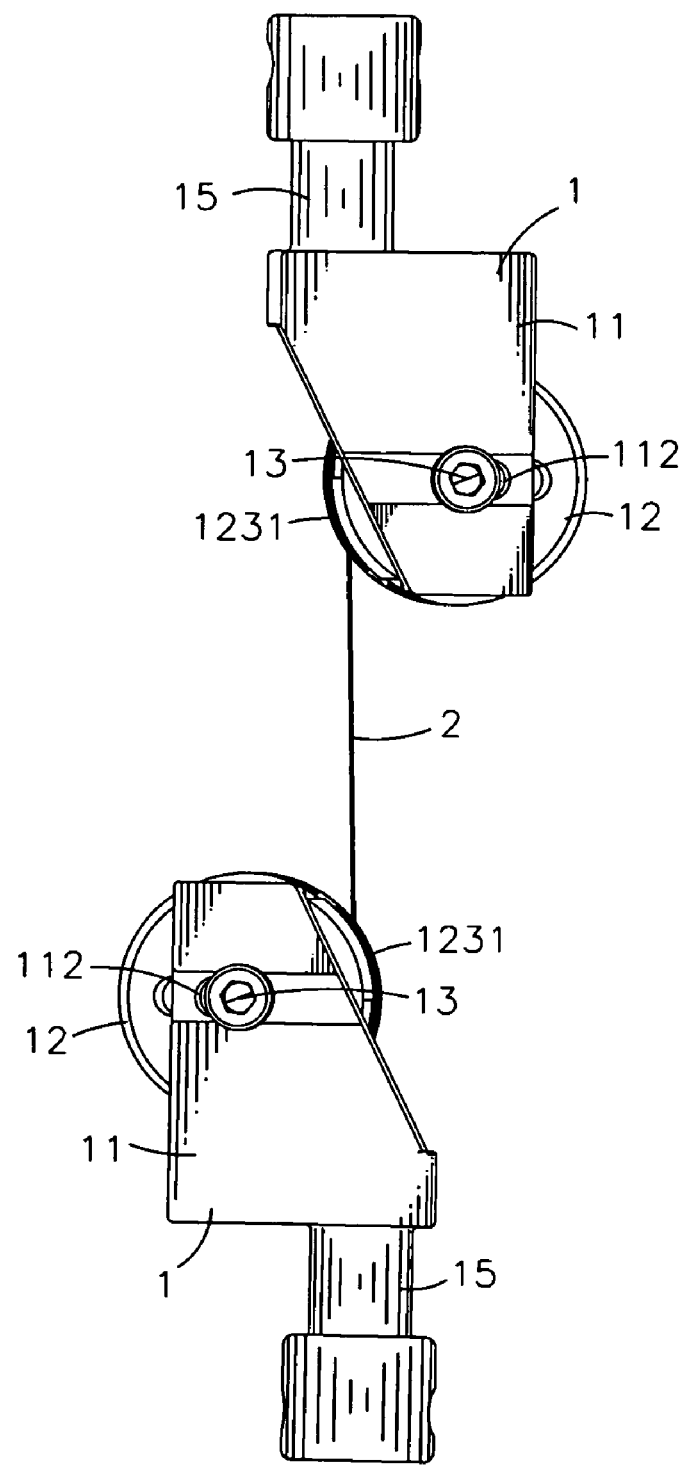
FIG. 3 is a plan view illustrating the wire pulled by two wire grips of the FIG. 2 along the reverse direction, wherein a measuring plate is removed from the wire grip.

Please referring to FIGS. 1-3, when the wire 2 is in test through the tension device, two end portions of the wire 2 are respectively fixed to the capstans 12 of two of the wire grips 1 mounted on the tension device. The capstans 12 are respectively adjusted to move in an appropriate distance so that the axis of the wire 2 between the wire grips 1 is consistent with the centerlines of the two holding components 15. That is, the pulling force provided by the tension device is in alignment direction with the pulling force received by a middle portion of the wire.

As described above, when the diameter of the wire 2 changes, the fixing component 13 is adjusted to move a corresponding distance in the adjusting hole 112. In the same time, the measuring plate 14 can be used as a scale to indicate the moving distance, which can makes the axis of the wire 2 be positioned exactly and quickly so as to conform with the pulling force. Thus the tension parameters of the wire 2 obtained during the testing process are exact and credible.

The foregoing description of the present invention has been presented for purposes of illustration and description. It is not intended to be exhaustive or to limit the invention to the precise form disclosed, and obviously many modifications and variations are possible in light of the above teaching. Such modifications and variations that may be apparent to those skilled in the art are intended to be included within the scope of this invention as defined by the accompanying claims

What is claimed is:

1. A wire grip for fastening a wire thereon and being mounted to and pulled by a tension device to receive a pulling force from the tension device to the wire, the wire grip comprising:
    a basic body mounted to the tension device; and
    a capstan slidably mounted to the basic body for fastening an end portion of the wire and enabling the wire to be wrapped thereon, the capstan being movable in a direction relative to an axis thereof whereby to ensure the pulling force provided by the tension device is in alignment direction with the pulling force received by a middle portion of the wire;
    wherein the basic body has a mounting plate disposed substantially parallel with the pulling force direction for holding the capstan thereon, the mounting plate defines an adjusting hole therethrough for receiving a fixing component which passes through the adjusting hole in a direction substantially perpendicular to the pulling force direction and then is fixed together with the capstan, the adjusting hole has a larger dimension in cross section than that of the fixing component for allowing the fixing component to be movable therealong, the mounting plate protrudes from one end thereof substantially perpendicularly to form a block, the capstan defines a gap at a portion thereof, and the block is blocked in the gap for preventing the capstan from rotating.

2. The wire grip as claimed in claim 1, wherein the mounting plate defines a groove at a surface thereof, the groove located above the adjusting hole and extending longitudinally in the movement direction of the fixing component for receiving a measuring plate with graduation printed on the measuring plate.

3. The wire grip as claimed in claim 1, the basic body further comprising a fixing plate intersecting with the mounting plate and adjacent to the capstan, the fixing plate defining a fixing hole therethrough for fixedly receiving one end of a holding component which is mounted to the tension device at the other end thereof.

4. The wire grip as claimed in claim 1, wherein the fixing component is screwedly connected to the capstan.

\* \* \* \* \*